(12) United States Patent
den Heeten et al.

(10) Patent No.: US 11,793,473 B2
(45) Date of Patent: Oct. 24, 2023

(54) SEAT ADAPTED FOR USE WITH A MAMMOGRAPHY APPARATUS

(71) Applicant: Teledyne Dalsa B.V., Eindhoven (NL)

(72) Inventors: Gerard Johan den Heeten, Enschede (NL); Cornelis Antonius Grimbergen, Enschede (NL)

(73) Assignee: Teledyne Dalsa B.V., Eindhoven (NL)

( * ) Notice: Subject to any disclaimer, the term of this patent is extended or adjusted under 35 U.S.C. 154(b) by 35 days.

(21) Appl. No.: 16/724,951

(22) Filed: Dec. 23, 2019

(65) Prior Publication Data
US 2020/0121268 A1    Apr. 23, 2020

Related U.S. Application Data

(63) Continuation of application No. PCT/NL2018/050407, filed on Jun. 25, 2018.

(30) Foreign Application Priority Data

Jun. 27, 2017  (NL) ........................................ 2019124

(51) Int. Cl.
*A61B 6/04*        (2006.01)
*A61B 6/00*        (2006.01)

(52) U.S. Cl.
CPC .......... *A61B 6/0478* (2013.01); *A61B 6/0414* (2013.01); *A61B 6/4411* (2013.01); *A61B 6/502* (2013.01)

(58) Field of Classification Search
CPC ... A61B 6/0414; A61B 6/0478; A61B 6/4411; A61B 6/502; A61B 6/506
See application file for complete search history.

(56) References Cited

U.S. PATENT DOCUMENTS

| 3,609,355 | A | * | 9/1971 | Schwarzer | ............. | A61B 6/502 |
| | | | | | | D24/158 |
| 4,941,709 | A | * | 7/1990 | Moller | .................... | A61G 15/02 |
| | | | | | | 297/325 |
| 5,099,503 | A | | 3/1992 | Strommer | | |

(Continued)

FOREIGN PATENT DOCUMENTS

| DE | 2014151 | * 12/1971 | ............... A61B 6/04 |
| DE | 2014151 A1 | * 12/1971 | ............... A61B 6/04 |

(Continued)

OTHER PUBLICATIONS

Machine translation of WO 2008043673 (Year: 2008).*

(Continued)

*Primary Examiner* — Dani Fox
*Assistant Examiner* — Soorena Kefayati
(74) *Attorney, Agent, or Firm* — Haynes and Boone, LLP

(57) ABSTRACT

A seat adapted for use with a mammography apparatus for detecting malignant cells in a breast of a patient. The seat includes an x-ray source and an x-ray detector for imaging the breast, and is provided to the mammography apparatus to enable the patient to sit during imaging. The seat is tiltable between at least two positions: a first position in which the seat is level with the horizon; and a second position in which the seat is tilted obliquely sideways with reference to the horizon. The seat may compress the breast during x-ray imaging of the breast with the x-ray source and the x-ray detector.

16 Claims, 1 Drawing Sheet

(56) References Cited

U.S. PATENT DOCUMENTS

| | | | |
|---|---|---|---|
| 5,335,257 A | 8/1994 | Stunberg | |
| 5,355,715 A | 10/1994 | Rausche et al. | |
| 5,590,166 A | 12/1996 | Suni et al. | |
| 5,820,552 A * | 10/1998 | Crosby | A61B 90/17 |
| | | | 600/407 |
| 5,999,836 A | 12/1999 | Nelson et al. | |
| 6,049,583 A | 4/2000 | Galkin et al. | |
| 6,694,173 B1 | 2/2004 | Bende et al. | |
| 7,558,367 B1 | 7/2009 | Tinwala et al. | |
| 7,656,993 B2 | 2/2010 | Hoering | |
| 7,734,013 B2 | 6/2010 | Kashiwagi et al. | |
| 8,397,731 B1 * | 3/2013 | Perper | A61B 6/0478 |
| | | | 128/845 |
| 8,406,846 B2 * | 3/2013 | Yoshizawa | G01T 1/1642 |
| | | | 600/407 |
| 8,464,378 B2 * | 6/2013 | Kuo | A61B 6/0435 |
| | | | 5/601 |
| 9,050,009 B2 | 6/2015 | Den Heeten et al. | |
| 9,743,997 B2 | 8/2017 | Grimbergen et al. | |
| 9,826,950 B2 | 11/2017 | Den Heeten et al. | |
| 2004/0116914 A1 * | 6/2004 | Dowlatshahi | A61B 18/20 |
| | | | 128/898 |
| 2005/0004458 A1 | 1/2005 | Kanayama et al. | |
| 2006/0245541 A1 | 11/2006 | Aubel | |
| 2006/0262903 A1 | 11/2006 | Diebold | |
| 2007/0121782 A1 | 5/2007 | Sendai | |
| 2008/0043904 A1 | 2/2008 | Hoernig | |
| 2008/0008066 A1 | 4/2008 | Kashiwagi et al. | |
| 2008/0080668 A1 | 4/2008 | Kashigawi | |
| 2008/0103387 A1 * | 5/2008 | Gross | A61B 6/4417 |
| | | | 600/564 |
| 2008/0024034 A1 | 10/2008 | Kashiwagi et al. | |
| 2008/0240346 A1 | 10/2008 | Kashiwagi et al. | |
| 2008/0249415 A1 | 10/2008 | Okamura et al. | |
| 2009/0026288 A1 | 10/2009 | Iordache et al. | |
| 2009/0262887 A1 | 10/2009 | Iordache et al. | |
| 2009/0304146 A1 | 12/2009 | Ramsauer | |
| 2010/0234727 A1 * | 9/2010 | Yoshizawa | A61B 6/0478 |
| | | | 600/431 |
| 2012/0020455 A1 | 1/2012 | Fischer | |
| 2012/0020464 A1 | 1/2012 | Matsuura | |
| 2013/0028373 A1 | 1/2013 | Den Heeten et al. | |
| 2013/0320234 A1 * | 12/2013 | Volokh | A61B 6/501 |
| | | | 250/453.11 |
| 2014/0328458 A1 | 11/2014 | Erhard et al. | |
| 2014/0341338 A1 | 11/2014 | Grimbergen et al. | |
| 2015/0043711 A1 * | 2/2015 | Den Heeten | A61B 6/0407 |
| | | | 378/37 |
| 2015/0208992 A1 * | 7/2015 | Marash | A61B 6/032 |
| | | | 600/407 |
| 2015/0265186 A1 | 9/2015 | Kuwabara | |
| 2016/0022364 A1 * | 1/2016 | Defreitas | A61B 6/502 |
| | | | 600/429 |
| 2017/0196748 A1 * | 7/2017 | Gaiser | A61G 13/08 |
| 2019/0231290 A1 | 8/2019 | Den Heeten et al. | |
| 2020/0107978 A1 * | 4/2020 | Laine | A61G 15/02 |
| 2021/0287409 A1 * | 9/2021 | Delmas | A61B 6/12 |

FOREIGN PATENT DOCUMENTS

| | | | |
|---|---|---|---|
| DE | 102006048607 | 4/2008 | |
| EP | 1493380 | 1/2005 | |
| EP | 2009465 | 12/2008 | |
| EP | 2754394 A1 | 7/2014 | |
| WO | 97/27801 | 8/1997 | |
| WO | 01/17424 | 3/2001 | |
| WO | WO-2008043673 A1 * | 4/2008 | A61B 6/0414 |
| WO | 2011/102713 | 8/2011 | |
| WO | 2013/076622 | 5/2013 | |
| WO | 2013/129920 | 9/2013 | |
| WO | 2013/162357 | 10/2013 | |
| WO | 2018/067005 | 4/2018 | |
| WO | 2019/004821 | 1/2019 | |
| WO | 2019/088826 | 5/2019 | |

OTHER PUBLICATIONS

Machine translation of DE2014151 (Year: 1971).*

Khamapirad, T., et al., "Diagnostic Imaging of Breat Cancer with LOIS: clinical feasibility", International Society for Optical Engineering, SPIE-INT, vol. 5697, No. 1, 2005, 35-44.

Mianohar, Sriang, et al., "Initial Results of in vivo Non-lnvasive Cancer Imaging in the Human Breast Using Near-Infrared Photoacoustics", Optical Express, vol. 15, No. 19, 2007, 12277-85.

Vaartjes, Susanne E., et al., "First Clinical Trials of the Twente Photoacoustic Mammoscope (PAM)", International Society for Optical Engineering, Proceedings SPIE, vol. 6629, 2007, 662917-1-662917-12.

Yoo, Ji Hoon, et al., "Silver Nanowire-Conducting Polymer-ITO Hybrids for Flexible and Transparent Conductive Electrodes with Excellent Durability", ACS Appl. Mater. Interfaces, vol. 7, 2015, 15928-15934.

* cited by examiner

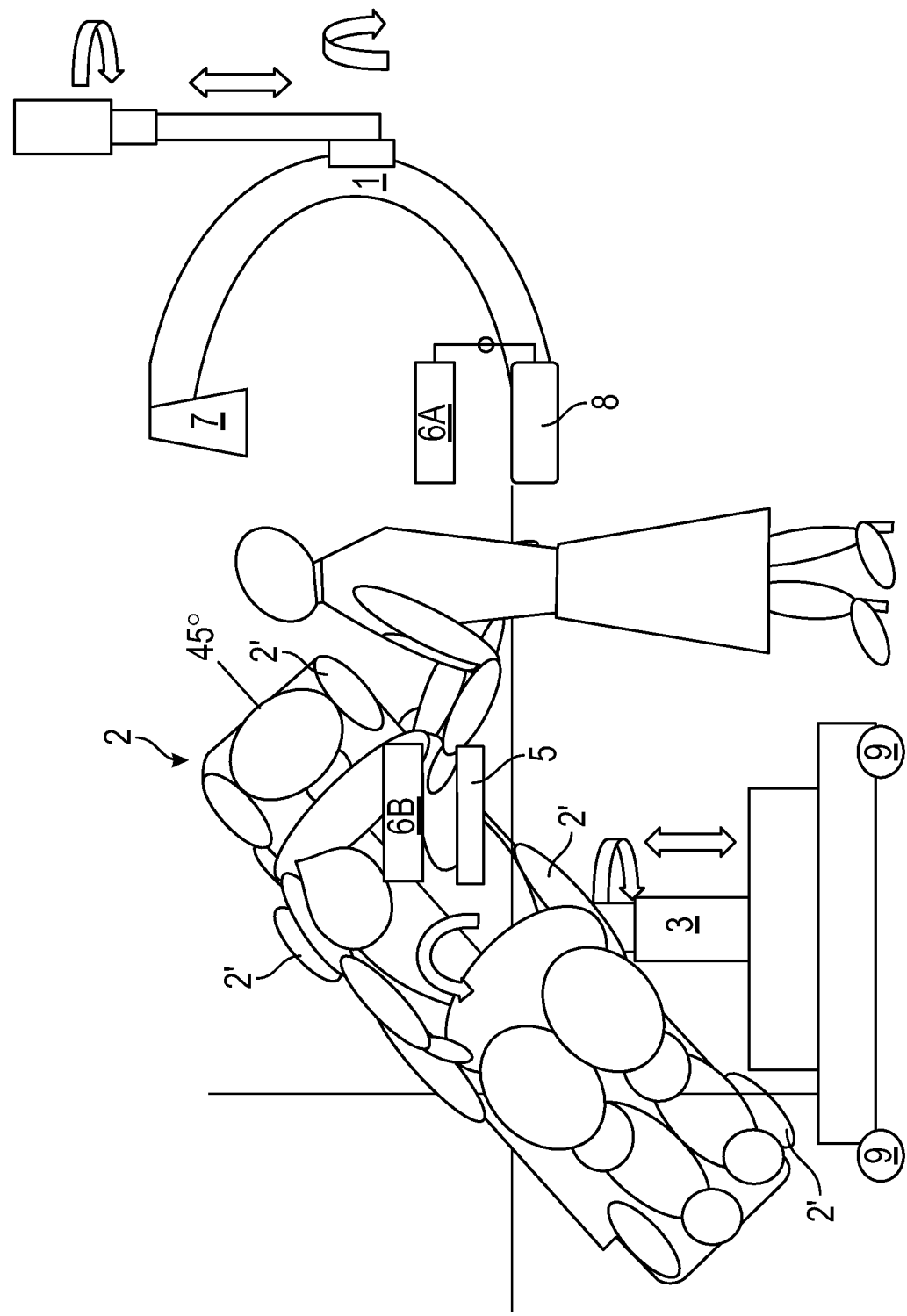

SEAT ADAPTED FOR USE WITH A MAMMOGRAPHY APPARATUS

CROSS-REFERENCE TO RELATED APPLICATIONS

This application is a continuation of International Patent Application No. PCT/NL2018/050407, entitled "SEAT ADAPTED FOR USE WITH A MAMMOGRAPHY APPARATUS", filed on Jun. 25, 2018, which claims priority to Netherlands Patent Application No. 2019124, entitled "SEAT ADAPTED FOR USE WITH A MAMMOGRAPHY APPARATUS", filed on Jun. 27, 2017, and the specification and claims thereof are incorporated herein by reference.

BACKGROUND OF THE INVENTION

The invention relates to a seat adapted for use with a mammography apparatus for detecting malignant cells in a breast of a patient, said mammography apparatus comprising an x-ray source and an x-ray detector for imaging the breast, wherein the seat is provided to the mammography apparatus to enable the patient to sit during imaging, and wherein the seat is tiltable between at least two positions, a first position wherein the seat is level with the horizon, and a second position wherein the seat is tilted obliquely sideways with reference to the horizon.

DE 2 014 151 discloses a seat and mammography apparatus. In DE 2 014 151 the seat is an integral part of the mammography apparatus. This limitation of the seat being an integral part of the mammography apparatus does however not apply to the instant invention, wherein the seat can also be an independent item although adapted for use with a mammography apparatus. DE 2 014 151 discloses two distinct screening modalities, a first one being parallel to a longitudinal body axis of the patient, and the second one being at right angles thereto. DE 2 014 151 is silent on a so-called medio lateral oblique screening of the breast which takes place at an angle of 45° with reference to the longitudinal body axis of the patient.

DE 10 2006 048 607 also discloses a seat and a mammography apparatus, wherein the seat is an integral part of the mammography apparatus. The seat of DE 10 2006 048 607 is tiltable in many directions except in a direction that enables a medio lateral oblique screening of the breast.

US2008/0103387 relates to a breast compression device comprising a seat, wherein the breast compression takes place to support an x-ray guided biopsy of the breast. The seat is tiltable backwards with the patient resting against the backrest of the seat in a backwards inclination.

EP 2 009 465 discloses a mammography apparatus with an integral seat, wherein the seat is tiltable to support the patient leaning forward. EP 2 009 465 does not support a medio lateral oblique screening of the breast.

U.S. Pat. No. 3,609,355 disclose a mammography apparatus wherein the x-ray source and x-ray detector are jointly rotatable to enable that imaging of the breast can be performed in different directions while the patient is sitting upright on a seat and the breast is presented by an operator (technician, radiographer, radiologist).

Like the other above-mentioned prior art, also U.S. Pat. No. 3,609,355 is silent on one of the most commonly applied imaging directions of the breast, being the MLO-screening or medio lateral oblique screening of the breast which takes place at an angle of 45° with reference to the longitudinal body axis of the patient. The other usual screening is the straight CC or craniocaudal screening of the breast which is in a direction parallel to the longitudinal body axis of the patient. Since in the MLO direction the most tissue is depicted, (the axillary tail included) the MLO is considered the most valuable measurement of the two.

Both with CC and with MLO screening the breast must be properly presented for an accurate and reliable imaging, that means without skin folds and without air inclusions that disturb the imaging. Particularly the MLO screening is then challenging since while the breast is compressed it is subject to not only the compression force, but also to gravity which makes it hard to maintain the breast stationary, free of skin folds and well-positioned during the imaging. For that reason the MLO screening requires complicated manipulations by the technician making it uncomfortable for the woman subjected to the screening. For the same reason the MLO screening provides severe working circumstances for the technician that operates the mammography apparatus and who has to secure the proper positioning of the breast during screening.

BRIEF SUMMARY OF THE INVENTION

It is an object of the invention to remove or alleviate these drawbacks and to make CC and MLO screening more easy, more reproducible, and with a higher quality, and comfortable for both the subjected woman and the technician.

According to embodiments of the present invention, a seat is proposed having the features of one or more of the appended claims.

According to an embodiment of the present invention, a seat is tiltable between at least two positions, a first position wherein the seat is level with the horizon, and a second position wherein the seat is tilted obliquely sideways with reference to the horizon at an angle of about 45°. Preferably, the seat comprises compression means for compressing the breast during x-ray imaging of the breast with the x-ray source and the x-ray detector. The breast can then always be reliably compressed during imaging without adverse influences from gravity, both in the first position as well as in the second position, wherein the first position corresponds to a CC screening and the second position corresponds to a MLO screening. Embodiments of the present invention therefore provide the advantage that the subjected woman can remain in the seat and be placed in the required position for either the CC screening or the MLO screening, whereas the technician is released from the laborious measures that are required in the prior art to secure a reliable imaging of the breast particularly in the MLO screening. Instead the technician can properly and in a relaxed way position the breast optimally prior to the imaging.

The benefits of embodiments of the present invention are thus particularly achieved due to the feature that the compression means have a fixed horizontal orientation and are movable to and from each other in a vertical direction for compressing the breast.

Beneficially the seat is preferably fixable in its position at an angle of about 45° with reference to the horizon to enable and secure a reliable simultaneous compression and imaging of the breast at an angle of about 45° with reference to a longitudinal body axis of the patient for executing a medio lateral oblique screening of the breast.

The patient's comfort is preferably promoted by arranging that a backrest of the seat is invariably in a plane that is transversally oriented with reference to the horizon. One possibility is that the backrest is rotated over part of a circle in a vertical plane.

The benefits of the invention are particularly promoted by providing that the compression means comprise a horizontal presentation table for supporting the breast while the patient is in the seat and while the seat is in either the first position or the second position, or between the first position and the second position.

Advantageously the seat is preferably provided with supports for the patient that are at least operational in the second position (MLO). It is preferred that in the second position of the seat these supports support the patient at least at the ankle, hip, armpit and head, and provide support to the then lowest arm of the patient.

To promote a proper and accurate positioning of the breast it is further preferred that the seat is movable up and down.

It is possible to embody the seat as a unitary or integral part of the mammography apparatus. In that situation the mammography apparatus can be simplified in that the x-ray source and x-ray detector can have a fixed vertical orientation with respect to each other, for example as a C-arc connected to the ceiling.

Another option is that the seat is removable from the apparatus and for example provided with wheels, preferably omnidirectional wheels. The seat can then also be applied with a more complicated existing mammography apparatus, wherein the x-ray source and x-ray detector are jointly rotatable, although this rotatability of the x-ray source and detector is then not required anymore for the MLO screening. Nevertheless it is then also possible that both the seat and the arc on which the x-ray source and detector are mounted are tilted so as to jointly provide that during MLO screening imaging of the breast occurs at an angle of 45° with reference to a longitudinal body axis of the patient, whilst the compression means have a fixed horizontal orientation. As an example, the arc and the seat can be tilted over about 30 degrees for the seat and about 15 degrees for the arc, or any other combination that adds up to about 45°.

Accordingly, embodiments of the present invention comprise a seat that is separate or separable from the mammography apparatus.

The seat itself, whether it is part of the mammography-apparatus or not, may be provided with a mechanism balancing the forces interacting with the breast of the patient. Using the technology disclosed in WO2013/162357 is recommended.

BRIEF DESCRIPTION OF THE SEVERAL VIEWS OF THE DRAWINGS

The accompanying drawing, which is incorporated into and forms a part of the specification, illustrates an embodiment of the present invention and, together with the description, serves to explain the principles of the invention. The drawing is only for the purpose of illustrating an embodiment of the invention and is not to be construed as limiting the invention. In the drawing:

FIG. 1 shows a mammography apparatus according to an embodiment of the present invention.

DETAILED DESCRIPTION OF THE INVENTION

In FIG. 1 a C-arm 1 is shown which is applied with a x-ray source 7 in top and x-ray detector 8 at the bottom of the C-arm 1. It further shows in FIG. 1 that a patient is sitting on a seat 2 which is rotatable, and which is shown after it has been turned from a first position wherein the seat 2 is level with the horizon towards a second position wherein the seat is tilted to the side and oblique with reference to the horizon at an angle of about 45° which corresponds to an MLO screening of the breast. The seat 2 can be fixed at this 45° tilted position with reference to the horizon. The seat 2 is further mounted on a telescopic stand 3 to enable its moving up and down for an accurate positioning of the breast. The FIGURE shows further a horizontal presentation table 5 on which the breast which is to be screened can in preparation of the screening be properly displayed for a most accurate and reliable imaging. The presentation table 5 is preferably X-ray transparent.

On its sides the seat 2 are preferably provided with supports 2' that are arranged on positions corresponding where the patient has the ankle, hip, armpit and head, and provide support to the then lowest arm of the patient.

In the FIGURE the seat 2 is shown as a separate item with wheels 9. This enables that the seat 2 can be used with any existing mammography apparatus. It is however also possible that the seat 2 is made a unitary or integral part of the mammography apparatus. In that case the conventional C-arm 1 can be simplified in that the x-ray source 7 and the x-ray detector 8 can be realized with a fixed vertical orientation with respect to each other.

It is remarked that reference 6A in the FIGURE refers to a paddle which is mounted on the C-arm 1, and which forms part of the compression means (together with the presentation table 5 for compressing the breast during x-ray imaging). It is also possible to embody the paddle on the seat 2 as is depicted in the FIGURE with reference 6B. 6A and 6B are therefore alternative options for placing the paddle. Preferably at all times the presentation table 5 of the seat 2, optionally completed with the paddle 6A, 6B on either the seat 2 or forming part of the mammography apparatus 1, is part of the compression means 5, 6A, 6B for compressing the breast during x-ray imaging of the breast with the x-ray source 7 and the x-ray detector 8.

In the embodiment wherein the compression means 5, 6B are entirely placed on the seat 2, that is when also the paddle 6B is mounted on the seat 2, the compression means 5, 6B have a fixed horizontal orientation and are movable to and from each other in a vertical direction for compressing the breast.

As already mentioned above the seat 2 is fixable at an angle of about 45° with reference to the horizon to enable a simultaneous compression and imaging of the breast at an angle of about 45° with reference to a longitudinal body axis of the patient for executing a medio lateral oblique screening of the breast. Furthermore, the FIGURE shows a backrest behind the back of the patient, and within the scope of the invention this backrest of the seat 2 is invariably in a plane that is transversely oriented with reference to the horizon.

Although the invention has been discussed in the foregoing with reference to an exemplary embodiment of the mammography apparatus of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

Note that in the specification and claims, "about" or "approximately" means within twenty percent (20%) of the numerical amount cited.

The invention claimed is:

1. A system for detecting malignant cells in a breast of a patient, comprising:
a seat that is tiltable between a first position, wherein the seat is level with a horizon and a second position, wherein the seat is tilted obliquely sideways with reference to the horizon; and
a mammography apparatus comprising an x-ray source and an x-ray detector,
wherein:
the seat comprises compression means for compressing the breast during x-ray B imaging of the breast with the mammography apparatus,
the compression means comprises a paddle and a table,
the compression means remain in a fixed horizontal orientation that is parallel to the horizon when the seat is in the second position, and
the paddle and the table are configured to move to and from each other in a vertical direction for compressing the breast.

2. The system according to claim 1, wherein in the second position, the seat is tilted at an angle of about 45° with reference to the horizon to enable a simultaneous compression and imaging of the breast for executing a medio lateral oblique screening of the breast.

3. The system according to claim 1, wherein the seat further comprises a backrest, and the backrest is in in a plane that is transversally oriented with reference to the horizon.

4. The system according to claim 1, wherein the table is configured to support the breast while the patient is in the seat and while the seat is in either the first position or the second position, or between the first position and the second position.

5. The system according to claim 1, further comprising a plurality of supports for the patient that are at least operational in the second position.

6. The system according to claim 1, wherein the seat is removable from the mammography apparatus and provided on wheels.

7. The system according to claim 1, wherein the seat is a unitary part of the mammography apparatus.

8. The system according to claim 5, wherein, in the second position of the seat, the plurality of supports support the patient at least at an ankle, hip, armpit and head, and provide support to a then lowest arm of the patient.

9. The system according to claim 6, wherein the wheels are omnidirectional wheels.

10. The system according to claim 7, wherein the x-ray source and x-ray detector have a fixed vertical orientation with respect to each other.

11. A seat adapted for use with a mammography apparatus, the seat comprising:
a backrest; and
compression means for compressing the breast during x-ray imaging of the breast with the mammography apparatus,
wherein:
the seat is tiltable between a first position, wherein the seat is level with a horizon and a second position, wherein the seat is tilted obliquely sideways with reference to the horizon,
the compression means comprises a paddle and a table,
the compression means remain in a fixed horizontal orientation that is parallel to the horizon when the seat is in the second position, and
the paddle and the table are configured to move to and from each other in a vertical direction for compressing the breast.

12. The seat of claim 11, wherein in the second position, the seat is tilted at an angle of about 450 with reference to the horizon to enable a simultaneous compression and imaging of the breast for executing a medio lateral oblique screening of the breast.

13. The seat of claim 11, wherein the backrest is in a plane that is transversally oriented with respect to the horizon.

14. The seat of claim 11, wherein the table is configured to support the breast while the patient is in the seat and while the seat is in either the first position or the second position, or between the first position and the second position.

15. The seat of claim 11, further comprising a plurality of supports for the patient that are at least operational in the second position.

16. The seat of claim 15, wherein, in the second position of the seat, the plurality of supports support the patient at least at an ankle, hip, armpit and head, and provide support to a then lowest arm of the patient.

* * * * *

UNITED STATES PATENT AND TRADEMARK OFFICE
CERTIFICATE OF CORRECTION

| | |
|---|---|
| PATENT NO. | : 11,793,473 B2 |
| APPLICATION NO. | : 16/724951 |
| DATED | : October 24, 2023 |
| INVENTOR(S) | : Gerard Johan den Heeten and Cornelis Antonius Grimbergen |

It is certified that error appears in the above-identified patent and that said Letters Patent is hereby corrected as shown below:

In the Claims

In Claim 1, Column 5, Line 15, change "x-ray B imaging" to --x-ray imaging--.

In Claim 3, Column 5, Line 30, change "in in a plane" to --in a plane--.

In Claim 12, Column 6, Line 27, change "450" to --45°--.

Signed and Sealed this
Twenty-third Day of January, 2024

Katherine Kelly Vidal
*Director of the United States Patent and Trademark Office*